United States Patent [19]

Adelberg

[11] Patent Number: 4,725,037
[45] Date of Patent: Feb. 16, 1988

[54] SHUT-OFF MECHANISM FOR CLAMP FOR REGULATING FLOW THROUGH PLASTIC TUBING

[76] Inventor: Marvin Adelberg, 16821 Oak View Dr., Encino, Calif. 91436

[21] Appl. No.: 34,637

[22] Filed: Apr. 6, 1987

[51] Int. Cl.⁴ .................. F16L 55/14; F16K 7/06
[52] U.S. Cl. ........................................ 251/6; 604/250
[58] Field of Search ............. 251/4, 6, 7; 604/250, 604/256

[56] References Cited

U.S. PATENT DOCUMENTS

| Re. 31,584 | 5/1984 | Adelberg | 251/6 |
| 3,918,675 | 11/1975 | Forberg | 251/6 |
| 4,013,263 | 3/1977 | Adelberg | 251/6 |
| 4,047,694 | 9/1977 | Adelberg | 251/6 |

*Primary Examiner*—George L. Walton
*Attorney, Agent, or Firm*—Edward A. Sokolski

[57] ABSTRACT

Tubing through which fluid flow is to be regulated is placed in a regulating clamp wherein it is clamped between a movable roller wheel and a surface of the clamp. Flow rate through the tubing is changed as determined by longitudinal adjustment of the position of the roller wheel. A full shut-off of flow through the tubing at a particular shut-off zone of the roller clamp is assured by means of ledge elements extending from the sidewall of the housing. These ledge elements, so as to provide a transitional deformation, are located in spaced relation to the clamping surface and are configured monotonically to provide a transitional and monotonically configured deformation of the tubing to avoid accidental rupture thereof, at the same time fully confining the tubing to prevent the formation of lumens in the peripheral edge portions thereof. In addition, full shut-off of the edge portion of the tubing is assured for parallel acting roller clamps, throughout the travel range of the wheel, if so desired. For inclined ramp roller clamps, improved tube confinement is offered.

5 Claims, 8 Drawing Figures

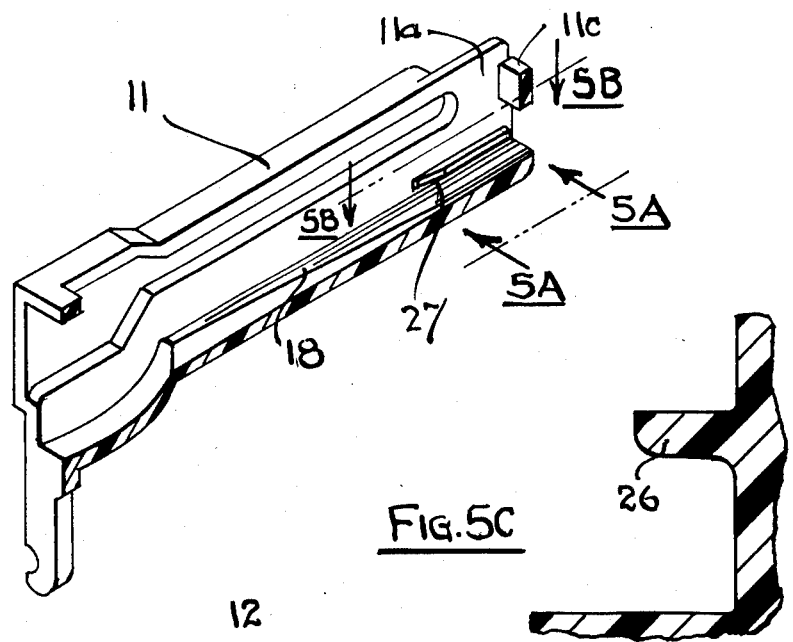
FIG. 4
FIG. 5C
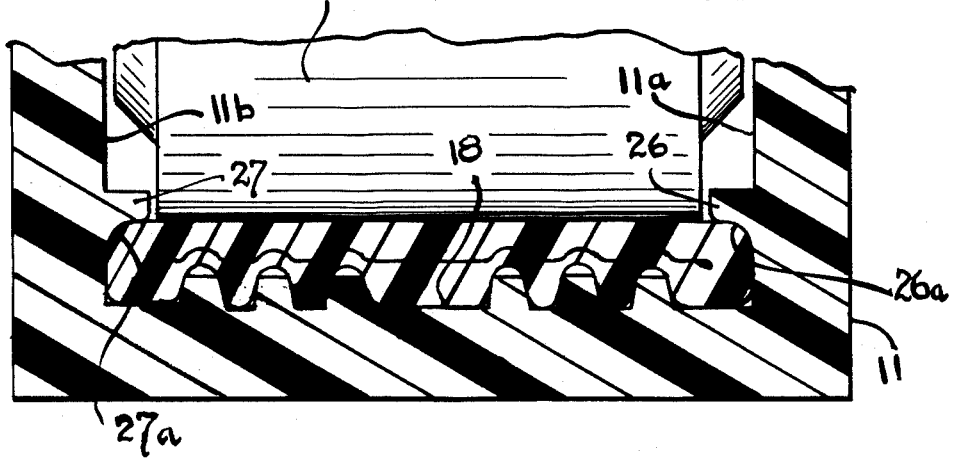
FIG. 5
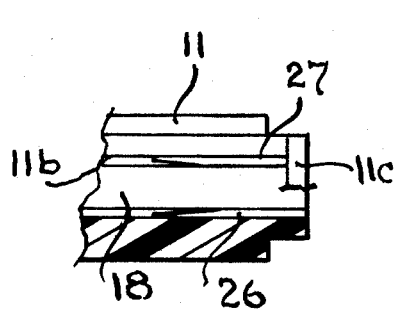
FIG. 5B
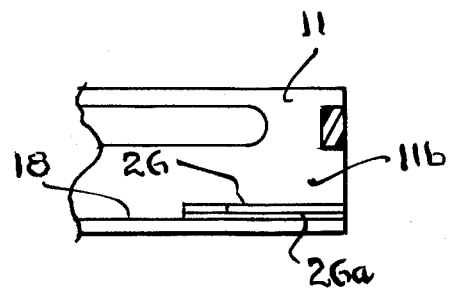
FIG. 5A

SHUT-OFF MECHANISM FOR CLAMP FOR REGULATING FLOW THROUGH PLASTIC TUBING

This invention relates to clamping devices for use in regulating fluid flow through plastic tubing and more particularly to such a device employing a roller wheel, which is adjusted along a generally longitudinal axis relative to an opposing clamping surface, to adjust and set the fluid flow rate.

In my U.S. Pat. Nos. Re 31,584, 4,013,263 and 4,047,694, clamping devices are described for regulating fluid flow through plastic tubing which are particularly useful in the administration of parenteral fluids. These devices have the advantage in that creep or cold flow of the plastic material of the tubing is minimized to provide a more constant rate of flow of the parenteral solution without the need for later readjustment once the initial setting has been made. A problem has been encountered, however, with these and other prior art devices in that it is difficult, where desired, to obtain a complete shut-off of all flow through the tubing under conditions to be described. In the case of the device of U.S. Pat. No. 4,047,694 this problem is attributable to a design characteristic which has desirable features with respect to flow control and resistance to tube tug abuse, but which introduces problems when the clamp is used to achieve flow shut-off by inviting the possibility of the formation of small lumens along the lateral peripheral portions of the tubing with full clamping action imposed on the central portions of such tubing. The same potential problem exists, to a lesser degree, where the gap between the corner of the adjustable wheel and the adjacent sidewall of the housing is not intentionally enlarged, but nonetheless exists, as is the case of the design of U.S. Pat. No. RE 31,584. Here again, there is a small gap or absense of a clamping surface in just the region where the tube is folded to have a short radius of curvature. For parallel acting clamps, lumens must not form in this region over the entire travel length of the wheel and should preferably be avoided because creep or cold flow will induce undesired flow rate variation. For inclined ramp clamps it may be desirable to have a predetermined distance between the roller and the opposing clamping surface or between the lateral raised element extension of the roller corner and the opposing clamping surface during flow control. Furthermore, in both the parallel acting and inclined roller types, it is critical that no lumens form in the tube shut-off zone.

This problem as well as the significance of the present invention are better appreciated by noting that large production quantities of clamps made in accordance with the designs of U.S. Pat. Nos. RE 31,584, 4,013,263 and 4,047,694 that were combined with tubing and which prodcued all the desired features of flow rate stability and tug resistance could not consistently achieve full shut-off with the wheel in its most forward position with the test fluid being water at pressures exceeding 20 p.s.i.g.

An attempt was made to solve this problem and clamps were sold in 1982 having raised lateral elements with a confining surface parallel to the clamping surface, and spaced therefrom. While this arrangement operated satisfactorily at lower liquid pressures, current requirements demand shut-off capability at water pressures in excess of 40 psi and this prior structure cannot meet the more stringent requirement presently imposed.

The aforementioned prior design utilized a lateral element in the complete shut-off zone having a confining surface facing and parallel to the clamping surface in the axial and transverse direction. The present invention utilizes a raised element confining surface, part or all of which is not parallel to the clamping surface in the transverse direction. Furthermore, for parallel acting clamps as well as for other clamp types, this non-parallel portion is always closer to the housing clamping surface as its distance from the nearest wheel edge increases. Simply modifying the aforementioned prior design to bring the lateral element to a location closer to the clamping surface would greatly increase the force needed to advance the wheel and would impose a greater danger of damaging the tubing. Further, with this design, it may not be possible to achieve full shut-off.

The desired improved result is achieved in the present invention by providing inwardly extending ledges on the inner sidewalls of the housing which provides clamping action on the laterally peripheral portions of the tubing. These ledges are tapered in a direction transverse to the tube or housing longitudinal axis, and contoured so as to provide a smooth transition on the clamping of the peripheral portions of the tubing to avoid damage to the tubing and located so as to provide the desired additional clamping action. The ledge or ledges are monotonically configured. As used herein, "monotonic" means that the ledge is configured such that as one moves laterally from the side face of the wheel to the adjacent wall of the housing, the effective distance between the under surface of the ledge and the clamping surface decreases over a portion of this travel and, over some portion, but not the entire distance, may be constant, and in no event does this effective distance increase. The monotonic configuration assures, as will be described, that there is little, if any, space for a lumen to form in the region where the sidewall and the underside of the ledge meet. The term "effective distance" is used to allow minor perturbations in the distance between the mean local clamping surface and the opposing mean local ledge surface. Such perturbations may be non-monotonic but are so small, that when compared with the mean distance, are small and this mean distance when averaged over a zone smaller that the tube wall thickness will decrease monotonically. Thus, "monotonic" as defined permits minor roughness to the surface which on a microscopic scale may not be technically monotonic. Again, it is to be noted that small deviations (on the order of a tube wall thickness) from a monotonic configuration will not significantly affect the performance of the device of the invention.

Hence, the present invention provides geometrically variable additional clamping action on the lateral peripheral edge portions of the tubing at a specified location.

The present invention has application to other (non-shut off) portions of clamps described in U.S. Pat. Nos. 4,013,263, 4,047,694, and RE 31,584 and even has application to other types of prior art clamps (e.g. inclined ramp clamps).

Two terms will initially be defined to facilitate a further discussion. A parallel acting clamp is here defined as one whereby the wheel throughout its travel fully pinches shut the tubing except for a portion of the tubing exposed to at least one relief groove. For this type of clamp, the tube lumen forms only in the tube portion exposed to this relief groove. Control is achieved by varying the ratio of the fully clamped shut tube portion to that unclamped portion exposed to the relief groove at any station of the roller by varying with wheel location the effective size of the relief groove to which the tubing is exposed, or by otherwise varying the relief or non pinched shut cross sectional area determined by the roller, parallel clamping surface and relief groove as the wheel location is changed.

An inclined ramp roll clamp is one which adjusts the tube lumen size by varying the distance between the wheel and its opposing clamping surface, the variation being achieved by causing the wheel axle to be guided by slots which are at an angle to the tube clamping surface. The inclined ramp clamp does not fully and tightly pinch shut or confine any portion of the tube over a range of travel of the wheel.

In the case of the parallel acting clamp, the wheel axle slots are substantially parallel to the tube clamping surface, but may have a small angle, provided this clamp otherwise meets the above-mentioned criteria for a parallel acting clamp.

The present invention may be also utilized to achieve a superior tube shut-off when the wheel is advanced to a zone at its travel extreme for the case of an inclined ramp roll clamp. As a further variation, this shut-off zone for the inclined ramp could have a clamping surface substantially parallel to the wheel travel. In all cases discussed, the present invention has substantial utility.

The new invention, or a variation thereof, may also be applied to that portion of the parallel acting clamp adjacent to where a lumen is intentionally formed. In this flow control application, the new invention assures that the tube is fully pinched shut in that section adjacent to the sidewall while, simultaneously relaxing (widening) the tolerance of the:
1. Wheel major diameter;
2. Wheel axle size;
3. Concentricity of the wheel major diameter and wheel axle;
4. Wheel clamping surface width.

For the embodiment of the present invention having lateral raised elements in the flow control section, the advantages of the device of U.S. Pat. No. 4,047,694 may be compromised or be rendered difficult to apply.

For the case of the inclined ramp roll clamp, the raised lateral elements of the present invention may be introduced at the location which generally follows the travel of the wheel edge portion closest to the clamping surface. In this case, the raised lateral elements could be parallel to the wheel axle guide. They also could be at an angle to the axle guide slot or the clamping surface. Applying the present invention to this case would permit a broader tolerance to the wheel width and provide desirable containment to the pinched tube.

It is therefore an object of this invention to enable the complete shut-off of flow in a clamp for regulating flow through plastic tubing which is especially desirable in extreme conditions such as when the fluid in the tube is at elevated pressure or has a low viscosity or surface tension.

It is a further object of this invention to provide an improved clamp for regulating flow through plastic tubing in which flow can be completely shut-off without hazard of damaging the tubing.

It is a still further object of this invention to provide a roller wheel clamp with a clamping or confining surface over most of that region where there would otherwise be a gap between the bottom corner of the wheel and the adjacent sidewall of the clamp housing.

Other objects of this invention will become apparent as the description proceeds in connection with the accompanying drawings of which:

FIG. 4 is a perspective view with partial cut away section illustrating the preferred embodiment;

FIG. 5 is a cross sectional view showing the ledge elements of the preferred embodiment fully clamping the peripheral portions of the tubing in the shut-off zone;

FIG. 5A is a side elevational view taken along the plane indicated by 5A—5A in FIG. 4;

FIG. 5B is a view taken along the plane indicated by 5B—5B in FIG. 4; and

FIG. 5C is an enlarged cross sectional drawing showing the details of the inwardly extending ledges of the device of the invention.

Figure 1:
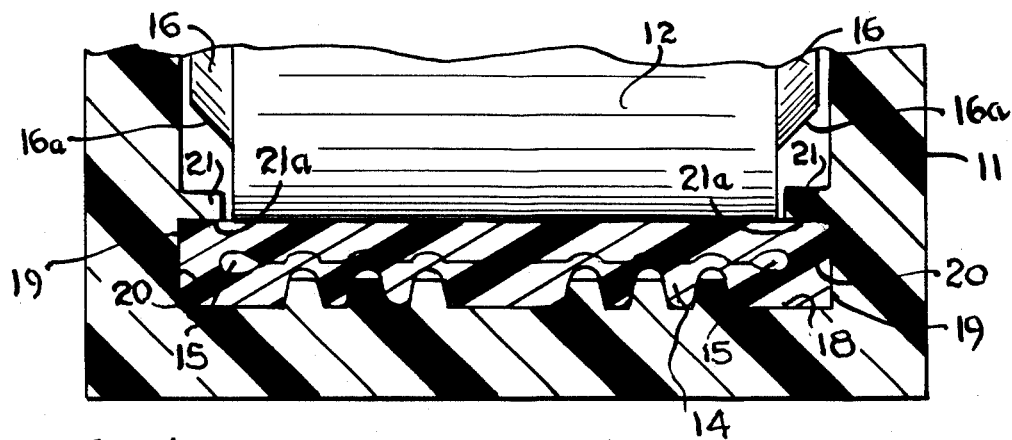
FIG. 1 is a schematic drawing illustrating a problem encountered in the prior art which the present invention overcomes.

Referring now to FIG. 1, a prior art device is shown in its fully "shut off" position. As can be seen, the tubing 14 is confined between housing 11 and wheel 12 with the central portions of the tubing being fully compressed but in the case of high fluid pressure or low surface tension with small undesirable lumens 15 being formed in the transversely peripheral edge portions of the tubing. In this prior art device, in an attempt to eliminate lumens 15, a pair of rectangular ledges 21 having planar undersurfaces 21a running parallel to clamping surface 18 were employed. It was found, however, that spaces 19 tended to form between the tubing 14, the ledges 21 and sidewall 20 which resulted in the formation of small flow lumens 15. Thus, in this case the tubing is not fully shut-off, as intended, but still permits some small fluid flow therethrough. This is partly because there is a larger radius of curvature or small deformation in the center section and a smaller radius of curvature or larger deformation combined with the absence of a clamping or confining surface at the peripheral cheek portions permitting high pressure or low surface tension leaks at these peripheral portions. Another significant factor in this device is the wheel shoulders 16 designed to improve resistance to tug abuse when the wheel is in the flow modulating mode or position. To assure that the peripheral portions are also fully confined or clamped shut, additional clamping means is required.

Figure 2:
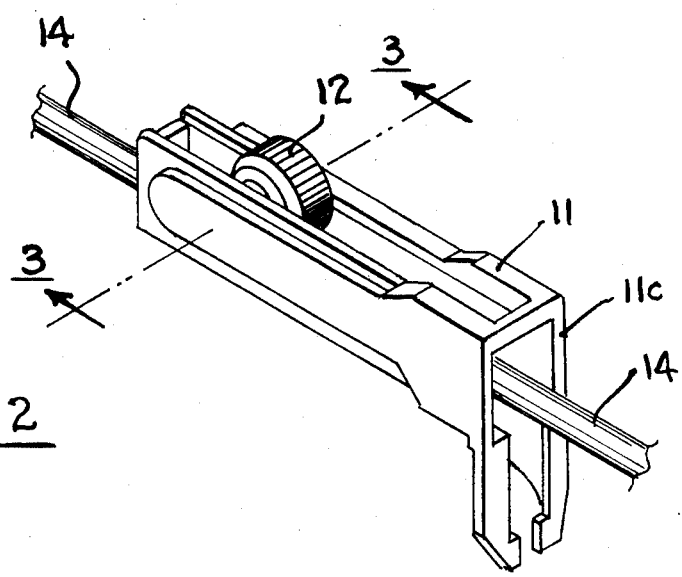
FIG. 2 is a perspective view illustrating a preferred embodiment of the present invention with the wheel entering the shut-off zone.
Figure 3:
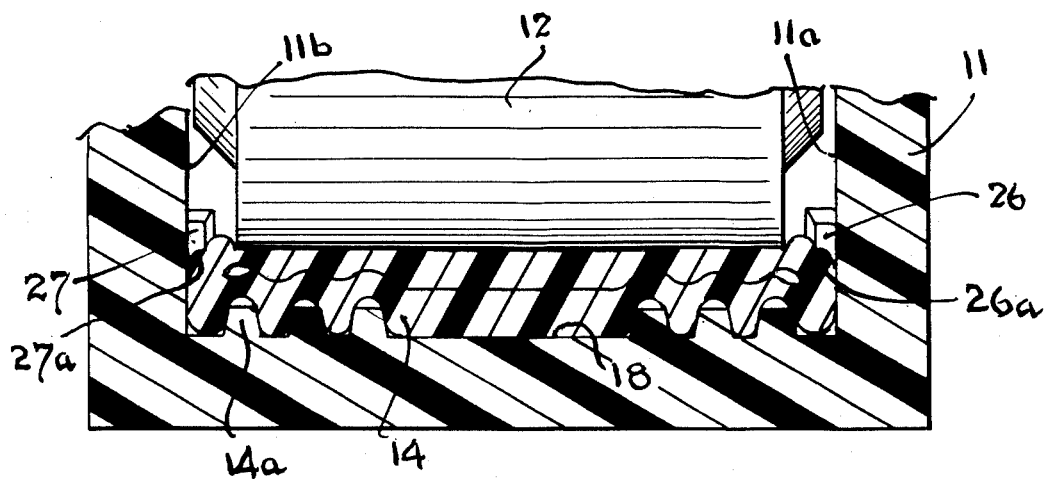
FIG. 3 is a cross sectional view taken along the plane indicated by 3—3 in FIG. 2.

Such additional clamping action is achieved as now to be described in connection with FIGS. 2-5. As shown in FIGS. 2 & 3 the clamp includes a housing 11 in which a roller wheel 12 is mounted. This roller wheel clamps plastic tubing 14 against a clamping surface 18. In the illustrative embodiment shown and described, the device except for the portions thereof relating to the present invention for full shut-off clamping is that described in my U.S. Pat. No. 4,047,694 issued Sept. 13, 1977, the disclosure of which is incorporated herein by reference. Referring particularly to FIGS. 3-5B a pair of ledge elements 26 and 27 extend inwardly from the inner sidewalls 11a and 11b of the housing. The lower surfaces 26a and 27a of these ledge portions are spaced and contoured so that they are either at a fixed distance or taper toward the clamping surface 18 when considered in a direction transversely away from the wheel direction of travel the clamping surface 18 being provided with spaced raised elements 14a as indicated. In accordance with this invention, the undersurfaces 26a and 27a of ledges 26 and 27 respectively are configured to be monotonic, that is, the distances between the undersurfaces 26a and 27a and the clamping surface 18 over a portion of the distance between the wheel edge and the sidewall decrease, rather than increasing or being flat and parallel over the entire distance, as was the case with the prior art designs. The effect is to eliminate or substantially reduce the presence of any space adjacent the undersurface of the ledge and the associated housing wall into which the outer peripheral and side of the tubing may move or flow in the full shut-off position, without imposing excessive forces on the tubing.

The use of a monotonic configuration for the undersurfaces 26a, 27a is important. For example, a flat parallel undersurface does not provide the performance herein described, nor does a configuration in which the distance between the undersurfaces and the clamping surface increases since this too allows for the presence of a space such that a flow lumen may form and if formed, may not be substantially eliminated. A portion of the undersurface may be curved, as shown, or a flat tapered surface may be employed, such that there is very little or essentially no space in the region between the ledge and the sidewalls and clamping surface for the tubing to creep or cold flow into, especially in the "shut-off" zone. Sharp corners which might cause damage to the tubing are carefully avoided, thus permitting smooth transition of the clamping action on the periphery of the tubing and also providing an increasing clamping action towards the outer edge of the tubing. Ledges 26 and 27 extend through a clamping shut-off zone such that as the wheel travels into this zone from the position shown in FIG. 3 the tubing is gradually brought to its full shut-off state as shown in FIG. 5. The wheel is kept centered by virtue of the axial taper of the entry portions of the ledge elements 26 and 27 which gradually brings them closer to the sides of the wheel as the wheel advances in the direction towards the end wall 11c. It is to be noted that for this embodiment the inner edges of undersurfaces 26a and 27a are substantially opposite the lower edges of wheel 12 as the wheel travels over its range, including the "shut-off" zone. Surfaces 26a and 27a taper to points which are at distances from the clamping surface 18 which decrease or remain constant as the distance of the points from the wheel edges increase.

The device of the invention can be utilized with clamps other than those described in my aforementioned patents or in any situation where additional clamping, confinement or full shut-off of flow through plastic tubing need be accomplished by advancing a roller wheel which clamps such tubing against a clamping surface in a confining housing; there otherwise being an undesirable lateral gap between the wheel corner and the lateral adjacent housing wall.

While the invention has been described and illustrated in detail, it is to be clearly understood that this is intended by way of illustration and example only and is not to be taken by way of limitation. The spirit and scope of the invention being limited only by the terms of the following claims.

I claim:

1. In a clamp for regulating fluid flow through plastic tubing having a housing with a longitudinal clamping surface against which the tubing is placed and at least one sidewall extending normally from said clamping surface, a roller wheel mounted in said housing opposite said surface for travel longitudinally relative thereto, the improvement whereby additional confinement or clamping of the lateral peripheral edge portion of the tubing is provided as the wheel travels towards its fully clamped shutoff position comprising:

a ledge element extending toward the center of the housing in the form of a projection from said one sidewall opposite and in proximity to said clamping surface, said ledge element running longitudinally along a portion of said sidewall adjacent to a portion of said clamping surface against which the opposing portion of the tubing is fully clamped shut, said ledge element having an undersurface directly opposite a portion of said clamping surface which is monotonically contoured transversely away from the wheel such that a lateral peripheral portion of the tubing is progressively clamped downwardly and radially inwardly between the ledge element and the clamping surface as the wheel advances to a position whereat said peripheral portion is further clamped against the ledge element undersurface and compressed between the wheel and the ledge element, thereby reducing any space adjacent to the undersurface of the ledge element to fully clamp the opposing portion of the tubing to shut-off.

2. The clamp of claim 1 wherein said wheel has similar undercut stepped shoulder portions on the opposite edges thereof defining recesses on the opposite edges of said wheel and said housing has opposing sidewalls extending normally from the opposite edges of said clamping surface, a second ledge element similar to said first mentioned ledge element extending from the other of said sidewalls towards said one sidewall whereby the lateral peripheral portions on the opposite sides of the tubing are clamped.

3. The clamp of claim 1 wherein said ledge element has a longitudinally tapered entry portion such that the ledge element gradually comes closer to the wheel as the wheel advances to the shut-off position, thereby keeping the wheel centered in the housing.

4. A roller clamp as set forth in claim 1 and further including a second ledge similar to said one ledge extending from the other of said sidewalls.

5. A roller clamp as set forth in claim 1 wherein the path of travel of said roller is substantially parallel to said clamping surface.

* * * * *